US012662934B2

(12) United States Patent
Jones et al.

(10) Patent No.: US 12,662,934 B2
(45) Date of Patent: Jun. 23, 2026

(54) CONTRAST COMPONENT COATING FOR SENSOR ANALYSIS

(71) Applicant: Halliburton Energy Services, Inc., Houston, TX (US)

(72) Inventors: Christopher Michael Jones, Katy, TX (US); James M. Price, Cypress, TX (US); Jian Li, Bellaire, TX (US); Darren George Gascooke, Houston, TX (US); William J. Soltmann, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 317 days.

(21) Appl. No.: 16/907,874

(22) Filed: Jun. 22, 2020

(65) Prior Publication Data

US 2021/0396133 A1 Dec. 23, 2021

(51) Int. Cl.

| | |
|---|---|
| ***E21B 47/135*** | (2012.01) |
| ***G01N 31/22*** | (2006.01) |
| ***G01N 33/28*** | (2006.01) |
| *G01N 21/77* | (2006.01) |

(52) U.S. Cl.

CPC ......... *E21B 47/135* (2020.05); *G01N 31/223* (2013.01); *G01N 33/287* (2013.01); *G01N 2021/7796* (2013.01)

(58) Field of Classification Search

CPC .... E21B 47/135; G01N 21/78; G01N 21/783; G01N 2021/7786; G01N 2021/7793; G01N 2021/7796; G01N 31/223; G01N 33/287; G01N 33/2823

See application file for complete search history.

(56) References Cited

U.S. PATENT DOCUMENTS

| | | | | |
|---|---|---|---|---|
| 9,297,767 | B2 | 3/2016 | Maida, Jr. et al. | |
| 10,025,000 | B2 | 7/2018 | Monteiro et al. | |
| 11,255,794 | B1 * | 2/2022 | Beshay | G01N 33/52 |
| 2010/0277740 | A1 * | 11/2010 | Hulteen | G01N 21/783<br>356/445 |
| 2012/0165626 | A1 * | 6/2012 | Irina | A61B 10/0064<br>600/316 |
| 2015/0122487 | A1 | 5/2015 | Lawrence et al. | |

(Continued)

FOREIGN PATENT DOCUMENTS

| | | | |
|---|---|---|---|
| DE | 102017100746 | B3 * | 8/2017 |
| WO | WO 2017/082891 | A1 | 5/2017 |
| WO | WO 2017/127411 | A1 | 7/2017 |

OTHER PUBLICATIONS

Hartle et al, Chemically Reversible Reactions of Hydrogen Sulfide with Metal Phthalocyanines, 2014, Inorganic Chemistry, 53, 15, 7800-7802 (Year: 2014).*

*Primary Examiner* — Elizabeth A Robinson
*Assistant Examiner* — Austin Q Le
(74) *Attorney, Agent, or Firm* — John Wustenberg; C. Tumey Law Group PLLC-HES

(57) ABSTRACT

A contrast device for analysis of a wellbore fluid includes: a substrate; and a contrast agent adhered to the substrate, wherein the contrast agent is configured to respond to an analyte within the wellbore fluid thereby altering a measurable characteristic of the contrast agent. A system including the contrast device may further include an energy source and a detector to facilitate measuring the characteristic of the contrast agent.

23 Claims, 6 Drawing Sheets

(56) References Cited

U.S. PATENT DOCUMENTS

| | | | | |
|---|---|---|---|---|
| 2015/0147231 | A1* | 5/2015 | Tscherner .......... | G01N 21/7703 422/82.07 |
| 2016/0041120 | A1 | 2/2016 | Ferguson et al. | |
| 2017/0115266 | A1* | 4/2017 | Ratulowski ............ | G01N 21/31 |
| 2017/0212272 | A1* | 7/2017 | Monteiro ........... | G01N 33/2841 |
| 2017/0307564 | A1 | 10/2017 | Shen et al. | |
| 2018/0104017 | A1* | 4/2018 | Heacock ................ | A61B 90/08 |
| 2020/0003697 | A1* | 1/2020 | Nakamura ........... | G01N 31/223 |
| 2021/0071517 | A1* | 3/2021 | Bane ................... | F16K 37/0058 |
| 2021/0108508 | A1* | 4/2021 | Edwards .................. | G01D 5/50 |

* cited by examiner

CONTRAST COMPONENT COATING FOR SENSOR ANALYSIS

FIELD OF THE DISCLOSURE

The present disclosure is related to sensor analysis of wellbore fluids. More particularly, the disclosure relates to a device, system, and method for utilizing a contrast component to expand sensor capabilities.

BACKGROUND OF THE DISCLOSURE

Components of wellbore fluids (including production fluids from subterranean formations as well as drilling fluids, stimulation fluids, workover fluids, etc.) may be measured or detected by optical, acoustic, NMR, dielectric, resistivity, or other sensors. Such measurements may be taken in situ (i.e., downhole) or at the wellbore surface. The presence of one or more components may dictate how the wellbore fluids are handled or processed. For example, hydrogen sulfide (H2S) is an extremely poisonous gas that can be lethal to workers at relatively low concentrations. As such, the detection and/or measurement of such components within the wellbore fluid is very important.

Each type of sensor is generally limited to operation within convenient energy ranges. For instance, although high energy ranges may increase the spectrum of detectable components, such high energy may be dangerous and/or may result in the need for frequent repair/replacement of the sensor. With optical sensors, a convenient energy range may comprise the visible, near-infrared, and mid-infrared wavelength ranges. However, many analytes are not active within these convenient ranges, or cannot be effectively measured or detected due to the presence of interferents (i.e., other components that are active within the same energy range).

DETAILED DESCRIPTION

Figure 1:
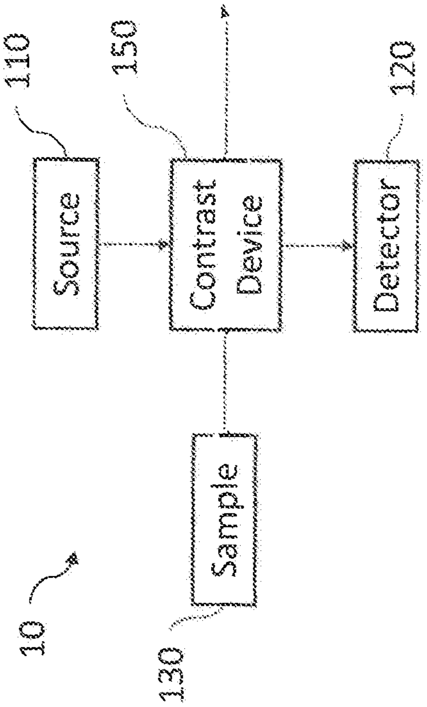
FIG. 1 is a diagrammatic illustration of a sampling system according to an embodiment of the present disclosure.

With reference to FIG. 1, a system 10 of the present disclosure includes an energy source 110 configured to transfer energy to or through a contrast device 150 that is in contact with a sample 130 containing an analyte to be measured and/or detected. A detector 120 is configured to receive energy from the contrast device 150 to thereby detect the presence of the analyte within the sample 130 and/or a concentration thereof.

The contrast device 150 includes a contrast agent that is configured to interact with the analyte within sample 130 and alter a property of the analyte and/or contrast agent, wherein the property is detectable by the detector 120. The detector 120 in probe or path contact with the contrast device 150 detects the change in analyte and/or contrast agent property and infer the analyte presence and/or concentration. The contrast agent and/or analyte may be positive or negatively influenced by the interaction between the contrast agent and the analyte. That is, the signal of the contrast agent and/or analyte may be enhanced, such as with indicators, or the signal may be suppressed, such as is the case with fluorescence quenching.

The contrast device 150 is configured to facilitate contact between the contrast agent and the analyte. According to one or more embodiments, the contrast device 150 is configured to be saturated by the sample 130. In such embodiments, the contrast device 150 may comprise a mesoporous substrate (i.e., a substrate containing pores with diameters between 2 and 100 nm or 2 and 50 nm). The contrast agent may be mixed or placed within the mesoporous substrate such that fluid components of the sample 130 are free to diffuse within the substrate.

Figure 2:
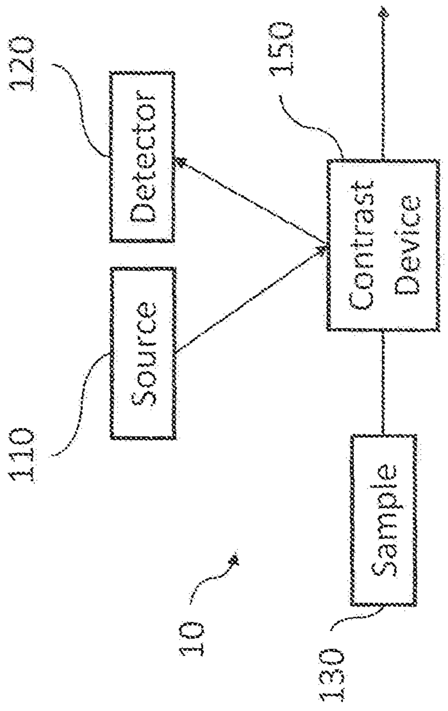
FIG. 2 is a diagrammatic illustration of a sampling system according to an embodiment of the present disclosure.

With reference to FIG. 2, in an alternative embodiment, the detector 120 and energy source 110 are positioned on the same side of the contrast device 150. In some embodiments, the detector 120 is offset from the energy source 110 by 0°, 30°, 45°, 60°, 90°, 120°, 135°, or 180° relative to the contrast device 150. In one or more embodiments, the system 10 includes a plurality of energy sources 110 that may be the same or different from one another. In one or more embodiments, the system 10 includes a plurality of detectors 120 that may be the same or different from one another. In some embodiments, the plurality of detectors 120 includes at least two detectors 120 positioned on opposites sides of the contrast device 150.

Figure 3:
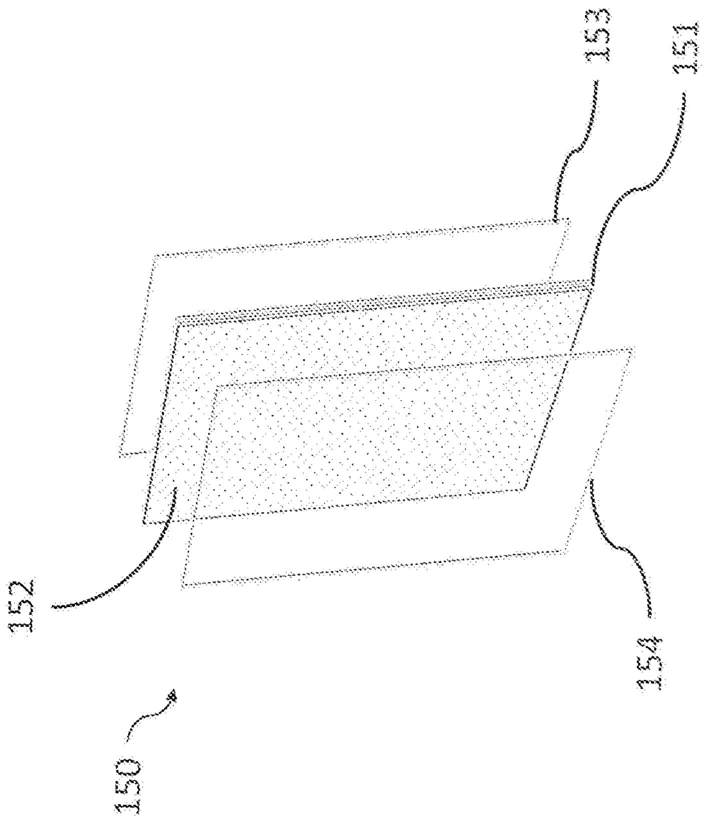
FIG. 3 is an exploded view of a contrast device according to an embodiment of the present disclosure.

In the embodiment shown in FIG. 3, the contrast device 150 includes a substrate 151 having a contrast agent 152 supported therein or thereon. The contrast device 150 may include one or more supports 153, 154 to support the substrate 151. The support 153, 154 is more resilient than the substrate 151. In one or more embodiments, one or both of supports 153, 154 are permeable to the sample 130. For example, the support 153, 154 may comprise a microparticle filter (e.g., a 1 to 150 micron mesh). In some embodiments, one of the supports 153, 154 is nonpermeable while the other support 153, 154 is permeable to the sample 130. In one or more embodiments, the support 153, 154 is selectively permeable to the analyte within the sample 130. In some embodiments, both supports 153, 154 are nonpermeable and the sample 130 contacts the substrate 151 along side edges between the supports 153, 154 or the sample 130 permeates through at least a portion of the substrate 151. In some embodiments, a support is not included in the contrast device 150. In some embodiments, only a single support 153, 154 is included in the contrast device 150. In some embodiments, a binder is used to adhere the substrate 151 to one or more supports 153, 154. According to one or more embodiments, the support 153, 154 comprises a transparent material, such as glass or plastic.

Figure 4:
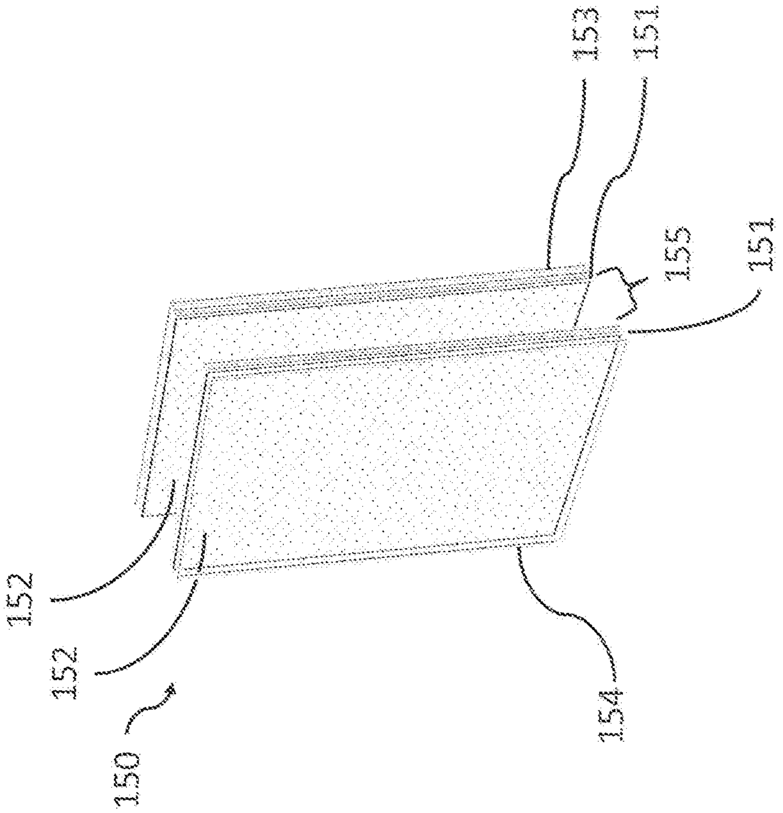
FIG. 4 is a diagrammatic illustration of a contrast device according to an embodiment of the present disclosure.

With reference to FIG. 4, the contrast device 150 comprises a plurality of substrates 151, each having a contrast agent 152 supported therein. The plurality of substrates 151 each have a space 155 therebetween to allow the sample 130 to penetrate the contrast device 150. In one or more embodiments, the detector 120 is positioned to face support 153 while energy source 110 is positioned to face support 154. In one or more embodiments, the detector 120 and energy source 110 are positioned to both face support 154 or both face support 153.

Figure 5:
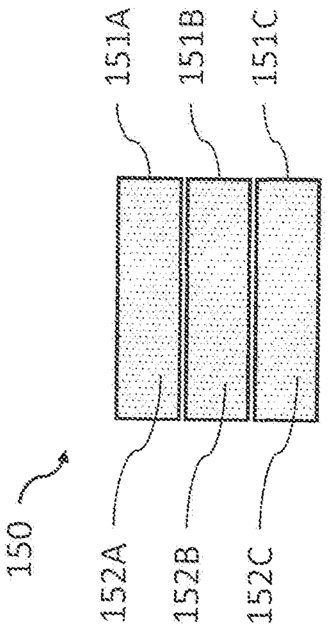
FIG. 5 is a diagrammatic illustration of a contrast device according to an embodiment of the present disclosure.

With reference to FIG. 5, the contrast device 150 may include one or more substrates 151A, 151B, 151C. Each substrate may include one or more contrast agents 152A, 152B, 152C. The respective substrates 151A, 151B, 151C may the identical or may vary in composition, size, etc. The respective contrast agents 152A, 152B, 152C may be identical. Each substrate 151A, 151B, 151C may include a plurality of contrast agents. In one or more embodiments, the contrast agents 152A, 152B, 152C are evenly distributed throughout the respective substrates 151A, 151B, 151C, present only at surfaces of the respective substrates 151A, 151B, 151C, or gradated through the substrates 151A, 151B, 151C. In any embodiments, each of substrates 151A, 151B, 151C includes at least one support.

According to one or more embodiments, the substrate 151 is a mesoporous substrate that comprises silanes or silicones. Many silanes and silicones are capable of crosslinking to form mesoporous structures. Crosslinking may be catalyzed (e.g., with metals or metal oxides), photo initiated (e.g., with UV light), or activated with additives. Crosslinked silanes and silicones are highly temperature stable and moderately to highly chemical resistant. Silanes and silicones are also highly capable of binding with various organic or inorganic compounds. When the system 10 is an optical system, the substrate of the contrast device 150 must be suited to transmit electromagnetic radiation. In this regard, silane and silicone resins and polymers may be transparent and have a suitable index of refraction. According to one or more embodiments, the contrast agent 152 is incorporated into the pore structure of the mesoporous substrate. In one or more embodiments, the contrast device 150 is prepared by mixing the contrast agent 152 into a liquid phase of a polymer precursor, followed by homogenization (e.g., via sonication). The mixture is then crosslinked to form a mesoporous substrate having the contrast agent 152 dispersed therein. In alternative embodiments, the contrast agent 152 may be impregnated into the mesoporous substrate.

In one or more embodiments, the contrast agent 152 is applied only to a surface of the substrate 151, wherein the substrate 151 may be a nonporous material such as glass. In such embodiments, the contrast agent 152 may be applied to the substrate 151 by, for example, chemical vapor deposition or physical vapor deposition.

In one or more embodiments, the substrate 151 includes a hydrophilic component, such as a hydrophilic silane or silicone. Hydrophilic silanes include but are not limited to: bis[(3-methyldimethoxysilyl)propyl]polypropylene oxixed-2-cyanoethyltriethoxysilane; N,N'-bis(3-trimethoxysilylpropyl)urea, 95%; tris(3-trimethoxysilylpropyl)isocyanate, tech-95; N-(triethoxysilylpropyl)-O-polyethylene oxide urethane (95%); N-(3-triethoxysilylpropyl)-4,5-dihydroimidazole; (3-trimethoxysilylpropyl)diethylenetriamine (tech-95); trimethoxysilylpropyl modified (polyethylenimine) (50% in isopropanol); dimethoxysilylmethylpropyl modified (polyethylenimine) (50% in isopropanol); aminopropylsilsesquioxane in aqueous solution; (3-acetamidopropyl)trimethoxysilane; N-3-[(amino(polypropylenoxy)] aminopropyltrimethoxysilane (60-65%); N,N'-bis-[(3-triethoxysilylpropyl)aminocarbonyl]polyethylene oxide (10-15 EO); 2-[methoxy(polyethyleneoxy)6-9propyl] trimethoxysilane (tech-90); N,N-bis(2-hydroxyethyl)-3-aminopropyltriethoxysilane (62% in ethanol); N,N'-bis(2-hydroxyethyl)-N,N'-bis(trimethoxysilylpropyl)ethylenediamine (66-68% in methanol); 2,2-bis(3-triethoxysilylpropoxymethyl)butanol (50% in ethanol); N-(3-triethoxysilylpropyl)gluconamide (30% in ethanol); N-(3-triethoxysilylpropyl)-4-hydroxybutyramide; carboxy ethyl silanetriol, disodium salt (25% in water); bis(methoxyethyl)-3-trimethoxysilylpropyl ammonium chloride (60% in methanol); (30-35% dodecylmethylsiloxane)-[7-10% hydroxy (polyethyleneoxy (6-9)propyl)methyl siloxane]-(55-65%; dimethyl siloxane) terpolymer (250-350 cSt); 3-(trihydroxysilyl)-1-propanesulfonic acid (30-35% in water); 3-(trihydroxysilyl)propyl methylphosphonate, monosodium salt (42% in water); 4-(trimethoxysilylethyl) benzyltrimethyl ammonium chloride (60% in methanol); N-(trimethoxysilylpropyl)ethylenediaminetriacetate, trisodium salt (35% in water); S-(trimethoxysilylpropyl)isothiouronium chloride (50% in water); and/or N-trimethoxysilylpropyl-N,N,N-tri-n-butyl ammonium bromide (50% in methanol). Hydrophilic silicones include but are not limited to: dimethylsiloxane-(60-70% ethylene oxide) block copolymer (20 cSt); dimethylsiloxane-[65-70%(60% propylene oxide/40% ethylene oxide)] block copolymer (1,800 cSt); dimethylsiloxane-(25-30% ethylene oxide) block copolymer (400 cSt); (30-35% dodecylmethylsiloxane)-[7-10% hydroxy (polyethyleneoxy (6-9)propyl)methyl siloxane]-(55-65% dimethyl siloxane) terpolymer, 250-350 cSt; (hydroxypropyleneoxypropyl)methylsiloxane-dimethylsiloxane copolymer (150-200 cSt); 0-allyloxy (polyethyleneoxy)triisopropoxytitanate (95%); N-(triethoxysilylpropyl)-O-polyethylene oxide urethane (95%); 2-[methoxy(polyethyleneoxy)6-9propyl]trimethoxysilane (tech-90); 3-[hydroxy(polyethyleneoxy)propyl]heptamethyltrisiloxane, 90%; 2-[methoxy(polyethyleneoxy)6-9propyl] heptamethyltrisiloxane, tech-90; 3-{2-[acetoxy (polyethyleneoxy)propyl]}heptamethyltrisiloxane, tech-95.

In one or more embodiments, the substrate 151 includes a hydrophobic component, such as a hydrophobic silane or silicone. Hydrophobic silanes include but are not limited to: octadecyl functional silane (sold under tradename SILICLAD, a registered trademark of Gelest); n-octadecyltrichlorosilane; isobutyltrimethoxysilane; (tridecafluoro-1,1,2,2-tetrahydrooctyl)trichlorosilane; (3,3,3-trifluoropropyl) trichlorosilane; heptadecafluoro-1,1,2,2-tetrahydrodecyltrichlorosilane. Hydrophobic silicones include but are not limited to: trimethylsiloxy terminated (25-35% methylhydrosiloxane)-dimethylsiloxane copolymer (25-35 cSt); hydride terminated polydimethylsiloxane (1,000 cSt); trimethylsiloxy terminated polydimethylsiloxane (1,000 cSt); chlorine terminated polydimethylsiloxane (sold under tradename AQUAPHOBE CM, a registered trademark of Gelest); chlorinated polydimethylsiloxane (sold under tradename AQUAPHOBE CF, a registered trademark of Gelest); diacetoxymethyl terminated polydimethylsiloxane (2,000-4,000 cSt).

When the contrast agent 152 is contained within a substrate 151, the substrate 151 may be configured to be saturated by the sample 130 in a predetermined amount of time (i.e., a saturation time). The saturation time may be controlled by, for example, the surface roughness, permeability, and/or thickness of the substrate 151. The degree of saturation may vary based on the application. For instance, if the system 10 only needs to identify the presence or absence of an analyte, the required degree of saturation may only be 10% or 20%. In other embodiments, the degree of saturation required may be, for example, at least 30%, at least 40%, at least 50%, at least 60%, at least 70%, at least 80%, at least 90%, at least 95%, or at least 99%. Consequently, the saturation time is the amount of time need to achieve the required degree of saturation.

The saturation time should not exceed a measurement time and in some embodiments may be no more than 50% of the measurement time. For example, if the measurement time is 30 minutes, the substrate 151 may configured such that the saturation time is less than 30 minutes or 15 minutes or less. The saturation time for a given substrate 151 may be calculated using diffusion laws, such as Darcy's law. Increased thickness of the substrate 151 may improve sensitivity but degrades response time. For mesoporous substances, assuming a sample 130 having a viscosity of 0.2-20 cP, the substrate 151 may have a thickness of 1-300 microns, 5-200 microns, 10-100 microns, or 20 to 50 microns.

Sensitivity of the system 10 may also be adjusted by varying the concentration of contrast agent 152 within the substrate 151. However, the amount of contrast agent 152 should not (1) exceed the maximum bound amount (i.e., the maximum amount that can be accommodated on or within the substrate 151) or (2) compromise of the substrate material properties, for example, the strength, crosslinking ability, linearity of response, pore size distribution, etc. In one or more embodiments, the contrast agent 152 may constitute 1 ppm to 1 wt %, 10-5000 ppm, 15-1000 ppm, 20-500 ppm, 25-100 ppm, or 50-500 ppm, based on the total weight of the contrast agent 152 and the substrate 151.

The contrast agent 152 is configured to interact with the analyte within sample 130 and alter a property of the analyte and/or contrast agent 152, wherein the property is detectable by the detector 120. Examples of optical contrast agents include dyes. In some embodiments, the optical contrast agent comprises a metal porphyrin, such as cobalt (II) phthalocyanine (CoPc). CoPc is responsive to aqueous hydrogen sulfide as shown in chemical reaction (1) below:

(1)

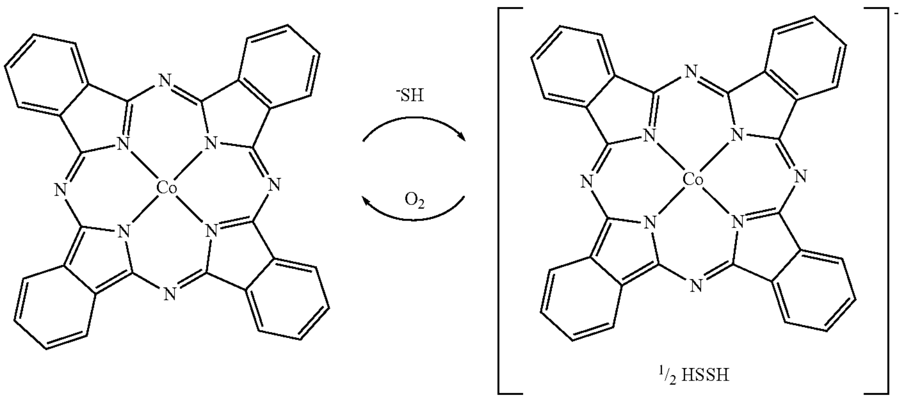

Other examples of porphyrins include those chelated with metal ions such as Gd, Mn, Fe, or Cu.

In one or more embodiments, the contrast agent may comprise zinc oxide, titanium oxide, copper (II) nitrate, and/or cobalt (II) nitrate. Examples of acoustic contrast agents include nano- or micro-glass/plastic bubbles having functionalized surfaces that act to shift resonant frequency.

In some embodiments, the contrast agent 152 may respond to components in the sample 130 other than the analyte. For example, a contrast agent sensitive to H2S may also respond to CO2. As such, incorporation of other contrast agents sensitive to the interferences may also be used to deconvolute the influence of the analyte. In some embodiments, a plurality of contrast agents 152 may be mixed within the contrast device 150. For example, the contrast device 150 may comprise a substrate 151 having a plurality of contrast agents 152 evenly distributed therethrough. In some embodiments, a plurality of contrast agents 152 may be juxtaposed in the contrast device 150. For example, distinct contrast agents 152 may be positioned in different portions of a single substrate 151 or may be separately incorporated into distinct substrates 151.

In one or more embodiments, the analyte is related to water chemistry, i.e., an ion dissolved in an aqueous sample 130. In one or more embodiments, the analyte comprises hydrogen sulfide. In one or more embodiments, the analyte comprises lead. In one or more embodiments, the analyte is pH of the sample.

According to one or more embodiments, the substrate is a disposable insertable structure, such as a cartridge, with respect to the sensor contact or path. For instance, if the system 10 is an optical system, then the substrate may be affixed to a glass slide support that may be placed into the optical path of the sample cell so that the sample 130 contacts the substrate side of the support.

The system 10 according to the present disclosure may be optical, dielectric, resistivity, acoustic, and/or NMR sensors for analyzing wellbore fluid (sample 130). The system 10 and method of using the same extends the use of these sensors to new applications by a relatively inexpensive modification of a flow line insert (contrast device 150). The system 10 may be used for production logging analysis (LWD) within a wellbore or downhole mud analysis while drilling or on wireline. During LWD operations, formation properties are measure during or shortly after drilling using tools integrated into the bottomhole assembly. The tools may include a pump to pull wellbore fluids into the tools. The fluid may then be analyzed using the system 10 described herein, which may be integrated into the tool and/or the bottomhole assembly. Similarly, the system 10 may be used with wireline logging, wherein tools carried by the wireline may be configured to introduce wellbore fluid to a contrast device 150 integrated into the tool and/or carried by the wireline. The system 10 may also be used to analyze production fluids (i.e., production logging), wherein production fluids flow from a completion zone into the wellbore. In any of the above, the wellbore fluid may be from a single completion zone or may be a mixture of fluids from a plurality of zones.

In one or more embodiments, the system 10 is an optical system and the energy source 110 is configured to transfer electromagnetic radiation through the contrast device 150, and the detector 120 is an optical sensor. The visible, near-infrared, and mid-infrared wavelength ranges are ill-suited to optically measure many analytes either because the components are not optical active in these wavelength ranges or because there is too much interference from other compounds in this wavelength range. Such analytes include most elemental ions (Na+1, K+1, Ca+2, Mg+2, H+1, Cl-1, Br-1, I-1, S-2 etc.), many polyatomic ions (SO4-2, CO3-2, HCO3-1, etc.), and other neutral components such as H2S, CO2, amines, etc. In other cases, trace components may be optically active and not highly interfered, but below the detection limit of conventional direct optical analysis. Using the contrast device 150 makes the optical system 10 able to measure these analytes. In one or more embodiments, the electromagnetic radiation includes one or more of ultraviolet, visible, near-infrared, and mid-infrared radiation. For example, the electromagnetic radiation may have a wavelength within the range of 10-8000 nm, 10-400 nm, 400-8000 nm, 400-750 nm, 750-2500 nm, and/or 2500 nm-8000 nm. In one or more embodiments, the optical sensor is a spectrometer, such as a spectrophotometer, spectrograph or spectroscope. In one or more embodiments, the optical sensor measures at least one optical property of electromagnetic radiation from the contrast device 150, such as absorption intensity, reflection, refraction, an absorbance spectrum, a fluorescence intensity, a fluorescence spectrum, or a shift in a peak absorption intensity. According to some embodiments, the measured property corresponds to an interaction between the contrast agent in the contrast device 150 and the analyte within the sample 130. The optical system may include a filter array or waveguide, for example, between the energy source 110 and the contrast device 150 and/or between the contrast device 150 and the detector 120.

In one or more embodiments, the system 10 is an acoustic system and the energy source 110 is configured to transfer sound energy to or through the contrast device 150 and the detector 120 is an acoustic sensor. According to one or more embodiments, the sound energy has a frequency of 0.1 Hz to 4 GHz, 0.1-20 Hz, 20-16000 Hz, 20-20000 Hz, and/or 0.020-4000 MHz. The acoustic sensor is configured to measure at least one property of the sound energy from the contrast device 150. In one or more embodiments, the acoustic sensor is a piezoelectric sensor. According to some embodiments, the measured property corresponds to an interaction between the contrast agent in the contrast device 150 and the analyte within the sample 130.

In one or more embodiments, the system 10 is a nuclear magnetic resonance system, the energy source 110 is configured to produce a magnetic field, and the detector 120 is an NMR sensor. According to some embodiments, one or more characteristics of the NMR spectrum corresponds to an interaction between the contrast agent in the contrast device 150 and the analyte within the sample 130. In one or more embodiments, the substrate 151 may be surrounded by a magnetic coil (not shown) to facilitate measurements of one or more property of the sample 130.

In one or more embodiments, the system 10 is a dielectric system, the energy source 110 is configured to transfer electricity to or through the contrast device 150, and the detector 120 is a dielectric sensor. The dielectric sensor is configured to measure at least one property of an electric charge from the contrast device 150. According to some embodiments, the measured property corresponds to an interaction between the contrast agent in the contrast device 150 and the analyte within the sample 130.

Figure 6:
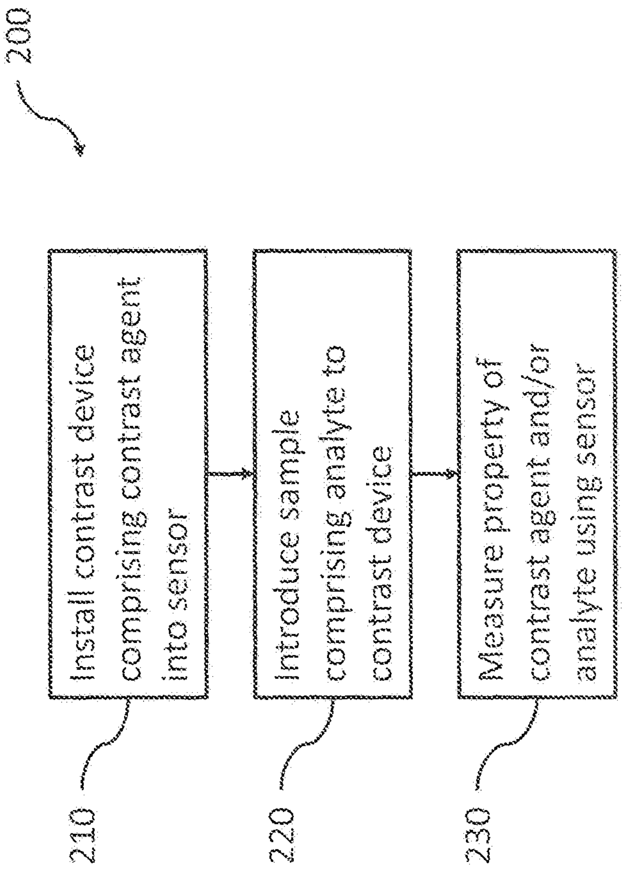
FIG. 6 is a diagram of a sample analysis method according to an embodiment of the present disclosure.

With reference to FIG. 6, a method 200 of analyzing a wellbore fluid (sample 130) includes a step 210 of installing contrast device 150 into a sensor. The contrast device 150 is as described above and comprises a contrast agent 152. The sensor may be, for example, the energy source 110 and the detector 120, as described herein. As such, step 210 may comprise installing the contrast device in contact with the detector 120 or in a probe path of the detector 120. In step 220, the sample 130 is introduced into the contrast device 150, wherein the analyte within the sample 130 is contact with the contrast agent 152 within the contrast device 150. In step 230, the detector 120 of the sensor measures a property of the analyte and/or contrast agent 152. After step 230, the method 200 may include making a decision regarding the handling of the wellbore fluid. For instance, the method 200 may analyze a small sample of wellbore fluid in order to inform decisions about a large quantity of the fluid. In response to the analysis, as least one drilling or production parameter may be adjusted. Additionally, the method 200 may include steps such as transmitting a signal from the detector 120 to the wellbore surface. Alternatively or additionally, the signal from detector 120 may be stored for review at the surface once the detector 120 has been retrieved from the well.

In one or more embodiments, the sample 130 may be analyzed downhole. In alternative embodiments, the substrate 151 containing the contrast agent 152 may be placed in a micro-sample chamber for inspection at the surface. The inner lining of such a micro-sample chamber may contain the substrate 151. Alternatively, the substrate 151 may be coated onto a removable portion of the micro-sample chamber. In some embodiments, the removable portion may be pressure sealed for ease of removal. The micro-sample chamber may have an optical conduit to a measurement point. Alternatively, the micro-sample chamber may be opened with the internal substrate 151 removed for inspection. Such removal may take place in an isolated containment area. Inspection may take place with a sensor device, such as but not limited to a digital camera, spectrometer, photometer, acoustic sensor, NMR sensor or dielectric sensor.

A contrast device for analysis of a wellbore fluid has been described herein. The contrast comprises: a substrate; and a contrast agent adhered to the substrate, wherein the contrast agent is configured to respond to an analyte within the wellbore fluid thereby altering a measurable characteristic of the contrast agent. The contrast device may further include any one or more of the following features: the substrate comprises a crosslinked silicone and/or a crosslinked silane; a support, wherein the substrate is adhered to the support; the support is a porous support having a mesh size of 1 to 150 microns; the contrast agent is dispersed throughout the substrate; and/or the contrast device is configured to be removably installed in a probe path of a wellbore sensor, wherein the wellbore sensor is an optical sensor, an acoustic sensor, an NMR sensor, a dielectric sensor, or a resistivity sensor.

A system for analysis of a wellbore fluid has been described herein. The system comprises: a wellbore fluid comprising an analyte; a contrast device in fluid communication with the wellbore fluid, the contrast device comprising: a substrate; and a contrast agent adhered to the substrate, wherein the contrast agent is configured to respond to the analyte thereby altering a characteristic of the contrast agent; an energy source configured to transfer energy to or through the contrast device; and a detector configured to detect or measure the characteristic of the contrast agent. The system may further include any one or more of the following features: the contrast device further comprises a support onto which the substrate is adhered and the contrast device is removably installed between the energy source and the detector; the analyte comprises H2S and the detector comprises an optical sensor; the contrast agent is a metal porphyrin; the energy source is configured to produce electromagnetic radiation having wavelengths from 400 nm to 8000 nm; the substrate comprises a crosslinked silicone and/or a crosslinked silane; and/or the contrast agent is dispersed within the substrate and the contrast agent constitutes 50-500 ppm based on a total weight of the contrast agent and the substrate.

A method of measuring an analyte in a wellbore fluid has been described herein. The method comprises: removably installing a contrast device within a probe path of a wellbore sensor, the contrast device comprising a substrate with a contrast agent adhere thereto, the contrast agent being configured to respond to the analyte thereby altering a characteristic of the contrast agent; contacting the wellbore fluid with the contrast device such that the analyte contacts the contrast agent; and measuring, using the wellbore sensor, the characteristic of the contrast agent. The method may further include any one or more of the following features: the wellbore sensor is an optical sensor, an acoustic sensor, an NMR sensor, a dielectric sensor, or a resistivity sensor; forming the contrast device, wherein forming the contrast device comprises mixing a silane or silicone prepolymer with the contrast agent to form a contrast agent mixture and crosslinking the contrast agent mixture; forming the contrast device further comprises after crosslinking the contrast agent mixture, adhering the crosslinked contrast agent mixture to a support or before crosslinking the contrast agent mixture, applying the contrast agent mixture to a support; the support is a porous support having a mesh size of 1 to 150 microns; removing and replacing the contrast device; and/or adjusting, in response to the measurement of the characteristic, at least one drilling or production parameter.

It is understood that variations may be made in the foregoing without departing from the scope of the disclosure. For instance, although the sample 130 has been described herein as being a fluid, the system 10 may be adapted for use with a solid sample 130.

In one or more embodiments, the elements and teachings of the various disclosed embodiments may be combined in whole or in part in some or all of the disclosed embodiments. In addition, one or more of the elements and teachings of the various disclosed embodiments may be omitted, at least in part, or combined, at least in part, with one or more of the other elements and teachings of the various disclosed embodiments.

Any spatial references such as, for example, "upper," "lower," "above," "below," "between," "bottom," "vertical," "horizontal," "angular," "upwards," "downwards," "side-to-side," "left-to-right," "left," "right," "right-to-left," "top-to-bottom," "bottom-to-top," "top," "bottom," "bottom-up," "top-down," etc., are for the purpose of illustration only and do not limit the specific orientation or location of the structure described above.

In one or more embodiments, while different steps, processes, and procedures are described as appearing as distinct acts, one or more of the steps, one or more of the processes, or one or more of the procedures may also be performed in different orders, simultaneously or sequentially. In one or more embodiments, the steps, processes or procedures may be merged into one or more steps, processes or procedures. In one or more embodiments, one or more of the operational steps in each embodiment may be omitted. Moreover, in some instances, some features of the present disclosure may be employed without a corresponding use of the other features.

Although several embodiments have been disclosed in detail above, the embodiments disclosed are not limiting, and those skilled in the art will readily appreciate that many other modifications, changes, and substitutions are possible in the disclosed embodiments without materially departing from the novel teachings and advantages of the present disclosure. Accordingly, all such modifications, changes, and substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112(f) for any limitations of any of the claims herein, except for those in which the claim expressly uses the word "means" together with an associated function.

What is claimed is:

1. A contrast device for determining at least one property of a wellbore fluid from a first contrast agent and at least a second contrast agent, the device comprising:

a disposable insertable structure comprising at least one crosslinked substrate;

a support, wherein the at least one crosslinked substrate is adhered to the support, wherein the support is selectively permeable to one or more analytes within the wellbore fluid, and wherein the support is more resilient than the substrate;

the first contrast agent adhered to at least one crosslinked substrate, wherein the first contrast agent is configured to respond to the one or more analytes thereby altering a measurable characteristic of the contrast device; and at least the second contrast agent juxtaposed in the contrast device and adhered to at least one crosslinked substrate, wherein the second contrast agent is configured to respond to the one or more analytes thereby altering a measurable characteristic of the contrast device, wherein the first contrast agent and the second contrast agent adhered to different locations on the crosslinked substrate, and wherein sensitivity of the second contrast agent to at least one of the one or more analytes is different from that of the first contrast agent.

2. The device according to claim 1, wherein the substrate comprises a crosslinked silicone and/or a crosslinked silane.

3. The device according to claim 1, wherein the first contrast agent is dispersed throughout at least one crosslinked substrate.

4. The device according to claim 3, wherein the support is a porous support having a mesh size of 1 to 150 microns.

5. The device according to claim 1, wherein the disposable insertable structure is removably installed in a probe path of a wellbore sensor.

6. The device according to claim 1, wherein a wellbore sensor attached to the disposable insertable structure is an acoustic sensor, an NMR sensor, a dielectric sensor, an optical sensor, or a resistivity sensor.

7. The device according to claim 1, wherein the substrate comprises a hydrophilic component.

8. The device according to claim 1, wherein the substrate comprises a hydrophobic component.

9. The device according to claim 1, wherein the substrate comprises at least one polymer.

10. The contrast device of claim 1, wherein the at least an analyte comprises at least one analyte selected from the group consisting of an elemental ion, a polyatomic ion, pH, a neutral component, and any combination thereof.

11. The contrast device of claim 1, wherein the at least an analyte comprises at least one analyte selected from the group consisting of Na, K, Ca, Mg, H, Cl, Br, I, S, $SO_4$, $CO_3$, $HCO_3$, $H_2S$, $CO_2$, an amine, and any combination thereof.

12. A system for determining at least one property of a wellbore fluid from a first contrast agent and at least a second contrast agent, the system comprising:

a wellbore fluid comprising at least an analyte;

a contrast device in fluid communication with the wellbore fluid, the contrast device comprising:

a disposable insertable structure comprising at least one crosslinked substrate;

a support, wherein the support is adhered to at least one crosslinked substrate, wherein the support is selectively permeable to at least one analyte, and wherein the support is more resilient than the substrate;

the first contrast agent adhered to at least one crosslinked substrate, wherein the first contrast agent is configured to respond to at least one analyte thereby altering a first measurable characteristic of the system;

at least the second contrast agent juxtaposed in the contrast device and adhered to at least one crosslinked substrate, wherein the second contrast agent is configured to respond to at least one analyte thereby altering the first and/or a second measurable characteristic of the system, wherein sensitivity of the second contrast agent to the at least one analyte is different from that of the first contrast agent, wherein the first contrast agent and the second contrast agent adhered to different locations on the crosslinked substrate;

an energy source configured to transfer energy to or through the contrast device; and a detector configured to detect or measure the first and/or the second measurable characteristic of the system.

13. The system according to claim 12, wherein the contrast device is a disposable insertable structure removably installed between the energy source and the detector.

14. The system according to claim 12, further comprising at least one wellbore sensor selected from the group consisting of an acoustic sensor, an NMR sensor, a dielectric sensor, and a resistivity sensor, and an optical sensor, wherein the first contrast agent comprises a metal porphyrin.

15. The system according to claim 14, wherein the energy source is configured to produce electromagnetic radiation having wavelengths from 400 nm to 8000 nm.

16. The system of claim 14, wherein the metal porphyrin is chelated with at least one metal ion selected from the group consisting of Gd, Mn, Fe, Cu, and any combination thereof, wherein the one or more analytes comprise hydrogen sulfide, wherein the metal porphyrin comprises cobalt (II) phthalocyanine, wherein the disposable insertable structure is a cartridge, wherein the contrast device is operable to deconvolute an influence of an interfering analyte, and wherein the cartridge is attached to a filter array or a waveguide.

17. The system according to claim 12, wherein the first contrast agent is dispersed within at least one crosslinked substrate in an amount between 50 and 500 ppm.

18. A method of determining at least one property of a wellbore fluid from a first contrast agent and at least a second contrast agent, the method comprising:

removably installing a contrast device within a probe path of a wellbore sensor, the contrast device comprising at least one crosslinked substrate with a support adhered thereto, wherein the contrast device comprises the first contrast agent and at least the second contrast agent juxtaposed in the contrast device, wherein a sensitivity of the first contrast agent is different than a sensitivity of the second contrast agent to one or more analytes of the wellbore fluid, the first contrast agent being configured to respond to the one or more analytes thereby altering a measurable characteristic of the contrast device, wherein the support is more resilient than the substrate, wherein the support is selectively permeable to at least one of the one or more analytes, and wherein the juxtaposition comprises at least the first and second contrast agents separately incorporated into distinct substrates;

contacting the wellbore fluid with the contrast device such that the one or more analytes contact the first contrast agent and at least the second contrast agent; and measuring, using the wellbore sensor, the altered measurable characteristic of the contrast device.

19. The method according to claim 18, wherein the wellbore sensor is an optical sensor, an acoustic sensor, an NMR sensor, a dielectric sensor, or a resistivity sensor.

20. The method according to claim 18, further comprising forming the contrast device, wherein forming the contrast device comprises:

mixing a silane or silicone prepolymer with at least the first contrast agent to form a contrast agent mixture; and crosslinking the contrast agent mixture.

21. The method according to claim 20, wherein forming the contrast device further comprises:

after crosslinking the contrast agent mixture, adhering the crosslinked contrast agent mixture to the support; or before crosslinking the contrast agent mixture, applying the contrast agent mixture to the support.

22. The method according to claim 18, further comprising removing and replacing the contrast device.

23. The method according to claim 18, further comprising adjusting, in response to the measurement of the characteristic, at least one drilling or production parameter.

* * * * *